(12) United States Patent
Herlerkson

(10) Patent No.: US 8,086,300 B2
(45) Date of Patent: Dec. 27, 2011

(54) ECG ELECTRODE CONTACT QUALITY MEASUREMENT SYSTEM

(75) Inventor: Earl C. Herlerkson, Cinebar, WA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 417 days.

(21) Appl. No.: 12/513,396

(22) PCT Filed: Nov. 2, 2007

(86) PCT No.: PCT/IB2007/054461
§ 371 (c)(1),
(2), (4) Date: May 4, 2009

(87) PCT Pub. No.: WO2008/056309
PCT Pub. Date: May 15, 2008

(65) Prior Publication Data
US 2010/0007413 A1    Jan. 14, 2010

(51) Int. Cl.
*A61B 5/04* (2006.01)

(52) U.S. Cl. ...................................... 600/509

(58) Field of Classification Search .............. 600/509, 600/523
See application file for complete search history.

(56) References Cited

U.S. PATENT DOCUMENTS

| | | |
|---|---|---|
| 4,917,099 A | 4/1990 | Stice |
| 5,020,541 A | 6/1991 | Marriott |
| 5,921,939 A | 7/1999 | Danielsson et al. |
| 2003/0083584 A1 | 5/2003 | Yonce |

FOREIGN PATENT DOCUMENTS

EP    1611845 A1    4/2006

*Primary Examiner* — Carl H Layno
*Assistant Examiner* — Paula J Stice
(74) *Attorney, Agent, or Firm* — W. Brinton Yorks, Jr.

(57) ABSTRACT

A system and method are provided for generating output signals indicative of contact quality of a plurality of electrodes coupled to a patient. A signal generator coupled to a reference electrode injects an alternating signal into the patient. A plurality of differential amplifiers, each coupled to a respective one of the plurality of electrodes to detect an input signal from the patient, are operable to output a respective output signal in response to a respective input signal. The output signal generated by the respective differential amplifier is indicative of contact quality for the respective electrode.

4 Claims, 5 Drawing Sheets

ECG ELECTRODE CONTACT QUALITY MEASUREMENT SYSTEM

BACKGROUND OF THE INVENTION

The present invention relates generally to the measurement of electrode contact quality for a multi-electrode diagnostic system capable of acquiring a patient electrocardiogram (ECG), and more particularly, to a measurement system that dynamically measures common mode rejection performance for the purpose of measuring electrode contact quality and accuracy of the ECG signal acquisition.

It is useful for the clinician who is applying ECG electrodes to a patient to know if the electrodes are properly connected to the patient. Prior art methods for measuring electrode contact status fall into two basic categories. One category is the application of a current to each of the individual electrodes individually. The second category is the application of a voltage to the patient that is common to all sense electrodes connected to the patient.

The input impedance of the typical ECG circuit is designed to be very high and, as a result, the application of a signal at each ECG input requires a very high source impedance current source. This current source can be either an alternating current (AC) signal or a direct current (DC) signal. One of the electrodes that is connected to the patient is a reference electrode. Typically, the reference electrode is the right leg electrode in a standard lead placement. The reference electrode is a low impedance connection from the patient to a measuring device configured to evaluate electrode contact quality based on the resulting voltage at each respective electrode. The return path for each current source is through the reference electrode. The voltage seen at each electrode is a function of the voltage drop at the reference electrode and the individual electrode.

A disadvantage of applying AC or DC current sources to each input is that this adds significant circuitry to each input at a point where high impedance design and board leakage is critical. Another disadvantage is that these techniques can incorrectly indicate that a lead wire is connected when it may actually be unconnected, if the input impedance of the cable or input amplifier is degraded due to a hardware failure or board leakage cause by ambient conditions of high humidity.

Another disadvantage of applying a DC current source to each input electrode is that DC currents can generate a voltage due to a current flowing through the electrolyte to metal interface of the electrode, creating a DC offset potential separate from the DC resistance of the skin contact impedance. This electrode potential can then be a source of noise if modulated by patient movement. To minimize DC offset potential, it is necessary to use very small DC currents on the order of 10 nA. However, such small currents are very difficult to implement reliably and board leakage in humid environments can potentially cancel such small currents and cause an incorrect reading. Another disadvantage of the DC current method is that the circuitry cannot differentiate between the DC offset potential of the gel to metal interface and that of the skin to electrode contact impedance. The DC current method is typically limited to detecting that the lead wire is connected but not a determination of the quality of the connection.

Applying a voltage at the reference electrode and measuring this voltage at the input lead wires is a much simpler method of verifying that the input lead wire is connected to the patient. This method can simply look at each lead wire individually to see if the signal amplitude is of an adequate level or can compare two or more lead wires differentially to see how well the common mode signal cancels. The voltage applied to the reference electrode would have to contain an AC component in order not to be confused by the DC offset potentials of each electrode.

A difficulty associated with the method of applying AC signals either as a current source or as a voltage at the reference electrode is the removal of the signals from the desired ECG signals. Pace pulse detection of internal pacemakers is typically a high bandwidth measurement of the input signal. Care must be taken not to affect this pace pulse detection outside the ECG bandwidth as well as not affecting the ECG signal inside the ECG bandwidth. Therefore, use of an AC signal for lead wire contact quality detection adds significant complexity in the signal processing necessary for accurate removal from the data that is then used for ECG and Pace Pulse signal processing.

SUMMARY OF THE INVENTION

In accordance with the principles of the present invention, a system is provided for generating output signals indicative of contact quality of a plurality of electrodes coupled to a patient. The system includes a signal generator coupled to a reference electrode and operable to output an alternating signal and a plurality of differential amplifiers. Each differential amplifier has a first input coupled to a respective electrode of the plurality of electrodes and further has a second input coupled to a floating common node. The differential amplifiers are operable to output a respective output signal in response to an input signal applied to the respective first input. The output signal is indicative of contact quality for the respective electrode.

Another aspect of the invention provides a system for generating output signals indicative of contact quality of a plurality of electrodes coupled to a patient. The system includes a signal generator coupled to a reference electrode and operable to output an alternating signal, and a differential array amplifier. The differential array amplifier is operable to output a respective output signal indicative of contact quality for a respective electrode. The differential array amplifier has a plurality of inputs and a corresponding plurality of differential amplifier stages. Each of the inputs is configured to be coupled to a respective one of the plurality of electrodes. Each differential amplifier stage includes a differential amplifier having a first input coupled to the respective input, a second input coupled to a first floating common node, and an output coupled to a second floating common node. The differential amplifier stages further include a first capacitor-resistor pair coupled in parallel between the output and the second floating common node, a second capacitor-resistor pair coupled in parallel between the second input and the second floating common node, and a third capacitor-resistor pair coupled in series between the second input and the first floating common node.

Another aspect of the invention provides a method of determining contact quality of a plurality of electrodes coupled to a patient. The method includes applying an alternating signal to the patient and detecting a respective input signal from the patient for each of the electrodes. Each of the electrodes is coupled to a first input of a respective differential amplifier and a second input of each differential amplifier is coupled to a floating common node. The method further includes generating a respective output signal in response to detecting the respective input signal and evaluating each of the respective output signals. Contact quality of an electrode is determined from a phase shift and attenuation of the respective output signal generated in response to the respective input signal.

DETAILED DESCRIPTION OF THE INVENTION

Certain details are set forth below to provide a sufficient understanding of the invention. However, it will be clear to one skilled in the art that the invention may be practiced without these particular details. Moreover, the particular embodiments of the present invention described herein are provided by way of example and should not be used to limit the scope of the invention to these particular embodiments. In other instances, well-known circuits, control signals, timing protocols, and software operations have not been shown in detail in order to avoid unnecessarily obscuring the invention.

Figure 1:
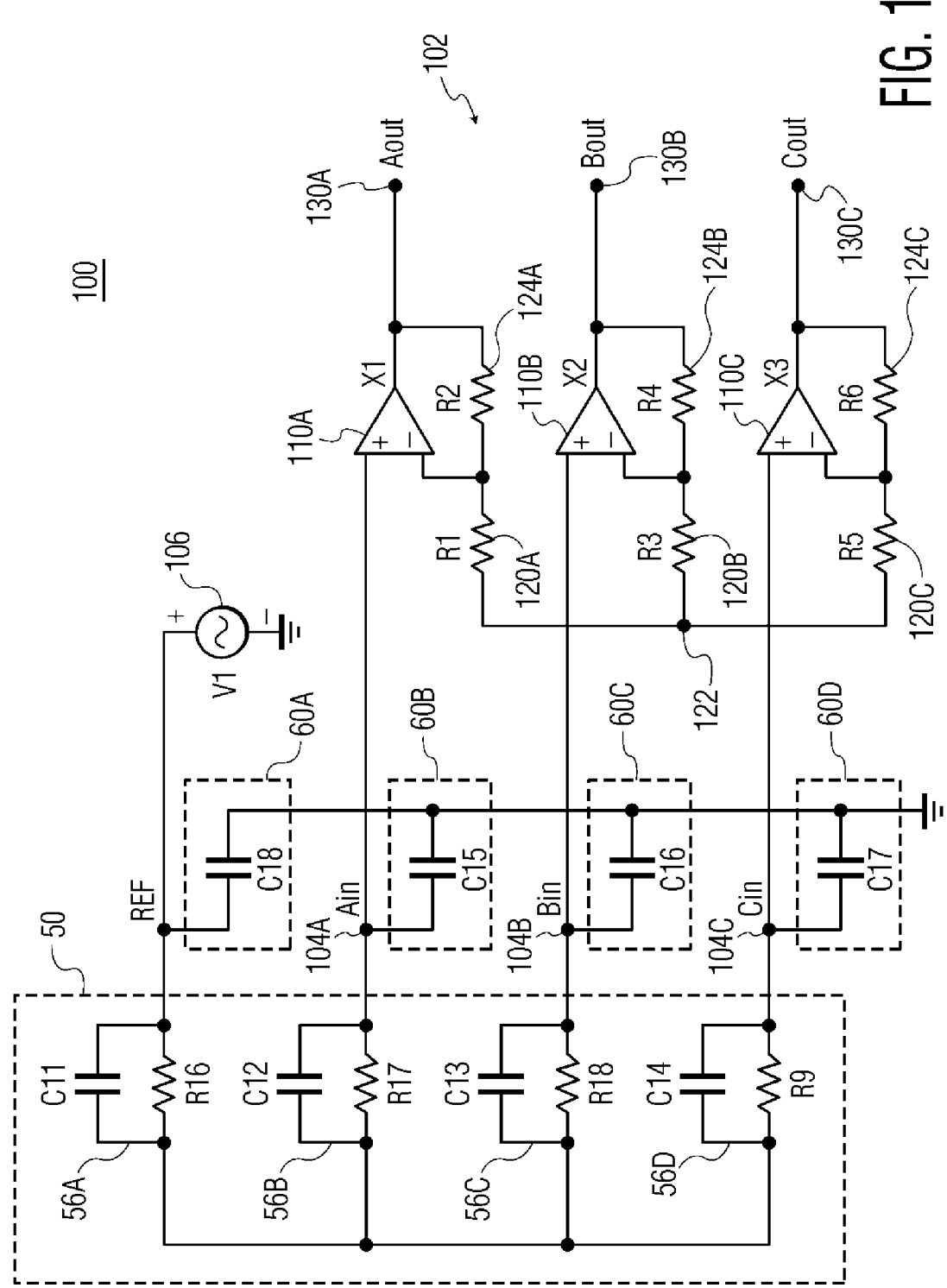
FIG. 1 is a schematic drawing of an electrode contact quality measurement system according to an embodiment of the present invention.

FIG. 1 illustrates an electrode contact quality measurement system 100 according to an embodiment of the present invention. The system 100 includes AC signal generator 106 for, as will be explained in more detail below, injecting a common mode AC signal V1 into a patient through a reference electrode REF. The system 100 further includes a differential array amplifier 102 configured for a four-electrode ECG circuit. The four electrodes include one reference electrode REF and three sensing electrodes. Alternative embodiments of the invention, however, can include greater or fewer electrodes for coupling to a patient. Although the particular embodiments described herein are for an application having four electrodes, it will be appreciated that the following description is sufficient to allow those ordinarily skilled in the art to practice embodiments having a different number of electrodes. Moreover, although the particular embodiments described herein are used for ECG systems, some or all of the principles of the present invention can be applied to other systems that measure patient biopotentials, for example, cardiographs, telemetry, Holter monitors, event monitors, defibrillators, and ultrasound systems having ECG capability.

The differential array amplifier 102 includes three operational amplifiers (op-amps) 110A-110C and associated gain setting feedback impedances, represented by resistors 120A-120C and 124A-124C. As will be described in more detail below, the resistors 120A-120C are preferably equal (R1=R3=R5) and the resistors 124A-124C are preferably equal (R2=R4=R6). The resistors 120A-120C are coupled to a floating common node 122. Each of the op-amps 110A-110C has a respective input node 104A-104C that is coupled through a respective electrode to receive electrical signals from a patient. The patient skin-electrode contact impedance is modeled in FIG. 1 by impedances 50, having four pairs of parallel resistor-capacitor circuits 56A-56D, each representing the impedance of one of the four electrodes coupled to the patient. Also shown in FIG. 1 are capacitors 60A-60D representing the ECG cable shield for each electrode.

In response to the input signals Ain, Bin, Cin from the patient electrodes, respective output signals Aout, Bout, Cout are generated by the op-amps 110A-110C and provided at output nodes 130A-130C. The Aout, Bout, and Cout signals are provided to a conventional analog-to-digital (A/D) converter (not shown) for converting the output signals into digital data representing the output signals. The digital data are evaluated by conventional processing circuitry (not shown) to determine whether any of the output signals exceed a threshold voltage. Where an output signal does exceed the threshold voltage, it is indicative of poor electrode contact.

The differential array amplifier 102 can be mathematically characterized by the following equations. Ain, Bin and Cin are equal to the voltage at input nodes 104A, 104B, and 104C, respectively, Aout, Bout and Cout are equal the voltage at output nodes 130A, 130B, and 130C, respectively, and the common node 122 is referenced as Com:

$$(Com-Ain)/R1+(Com-Bin)/R3+(Com-Cin)/R5=0, \qquad (1)$$

$$Com*(1/R1+1/R3+1R5)=Ain/R1+Bin/R3+Cin/R5, \qquad (2)$$

$$Com=(Ain/R1+Bin/R3+Cin/R5)/(1/R1+1/R3+1R5), \qquad (3)$$

$$Com=Ain/(1+R1/R3+R1/R5)+Bin/(1+R3/R1+R3/R5)+ \\ Cin/(1+R5/R1+R5/R3). \qquad (4)$$

Equation (4) results from equation (1) as it is expanded through equations (2) and (3). Additionally, $$Aout=Com+(Ain-Com)*(R2+R1)/R1, \qquad (5)$$

$$Bout=Com+(Bin-Com)*(R4+R3)/R3, \text{ and} \qquad (6)$$

$$Cout=Com+(Cin-Com)*(R6+R5)/R5. \qquad (7)$$

Assuming that R1=R3=R5 and R2=R4=R6, equation (4) reduces to:

$$Com=(Ain+Bin+Cin)/3. \qquad (8)$$

Applying equations (5), (6), and (7), $$Aout-Bout=(Ain-Bin)*(R2+R1)/R1, \qquad (9)$$

$$Aout+Bout+Cout=Ain+Bin+Cin. \qquad (10)$$

As shown by equation (8), the voltage at the common node 122 is the average of the voltages at the input nodes 104A-104C, and is independent of the values of resistors 120A-120C and 124A-124C. Moreover, as shown by equations (9) and (10), the differential gain (Adm) is equal to (R2+R1)/R1 and the common mode gain (Acm) is unity. As a result, the common mode rejection of the differential array amplifier 102 is equal to the differential gain.

In operation, an AC voltage V1 is delivered to the patient through reference electrode REF and the differential array amplifier 102 detects the AC signal as input signals for the ECG channels. The differential array amplifier 102 dynamically measures the common mode rejection capability of the complete ECG measurement system while it is connected to the patient. Degraded common mode performance, as manifested by a different input gain or frequency response for one electrode than for another electrode, is an indication that the quality of the contact of an electrode is poor. The change in input gain or frequency response occurs when the electrode contact impedance is large enough such that the input impedance of the ECG system begins to cause phase shift and/or attenuation of the signal.

An advantage of using a differential amplifier is that the common mode signal due to the AC voltage injected through the reference electrode REF is significantly reduced in amplitude so that for electrodes with good contact impedance, the signal is less than the required noise performance of the system. However, when the electrode contact impedance exceeds a level that distorts the ECG signal, the differential array amplifier 102 amplifies a difference signal to a level that exceeds the system noise level and can be detected. This reduces the complexity and simplifies the requirement for removal of the AC signal used to detect the lead contact quality.

By using the differential array amplifier 102 and an injected AC reference signal, the same characteristics that affect the accuracy of ECG acquisition are measured, regardless of potential changes of the input impedance of the ECG system. If the input impedance of the cable or input electronics are degraded, this will not result in a false indication that the electrode is connected when in reality it is not. The system correctly accounts for the degraded input impedance and will not indicate a good connection if the electrode contact impedance is significantly lower than the degraded circuit input impedance. As a result, the output signals of the differential array amplifier 100 will indicate that the leads are adequately connected only if the measurement quality is good, and will not falsely indicate that the contact is bad unless the measurement is really at risk of being inaccurate.

The AC signal injected into the patient through the reference electrode REF may be of any waveform or frequency. In alternative embodiments, the common mode signal is generated by a random or pseudo-random noise source. The frequency of the AC signal can be selected to be inside the ECG band in order to measure the signal quality at desired ECG frequencies rather than limiting it to a value outside of the ECG band. The common mode signal is preferably small in amplitude so that it will cancel out of the differential signal when the contact quality is good and become apparent when the electrode contact quality is poor.

Figure 2:
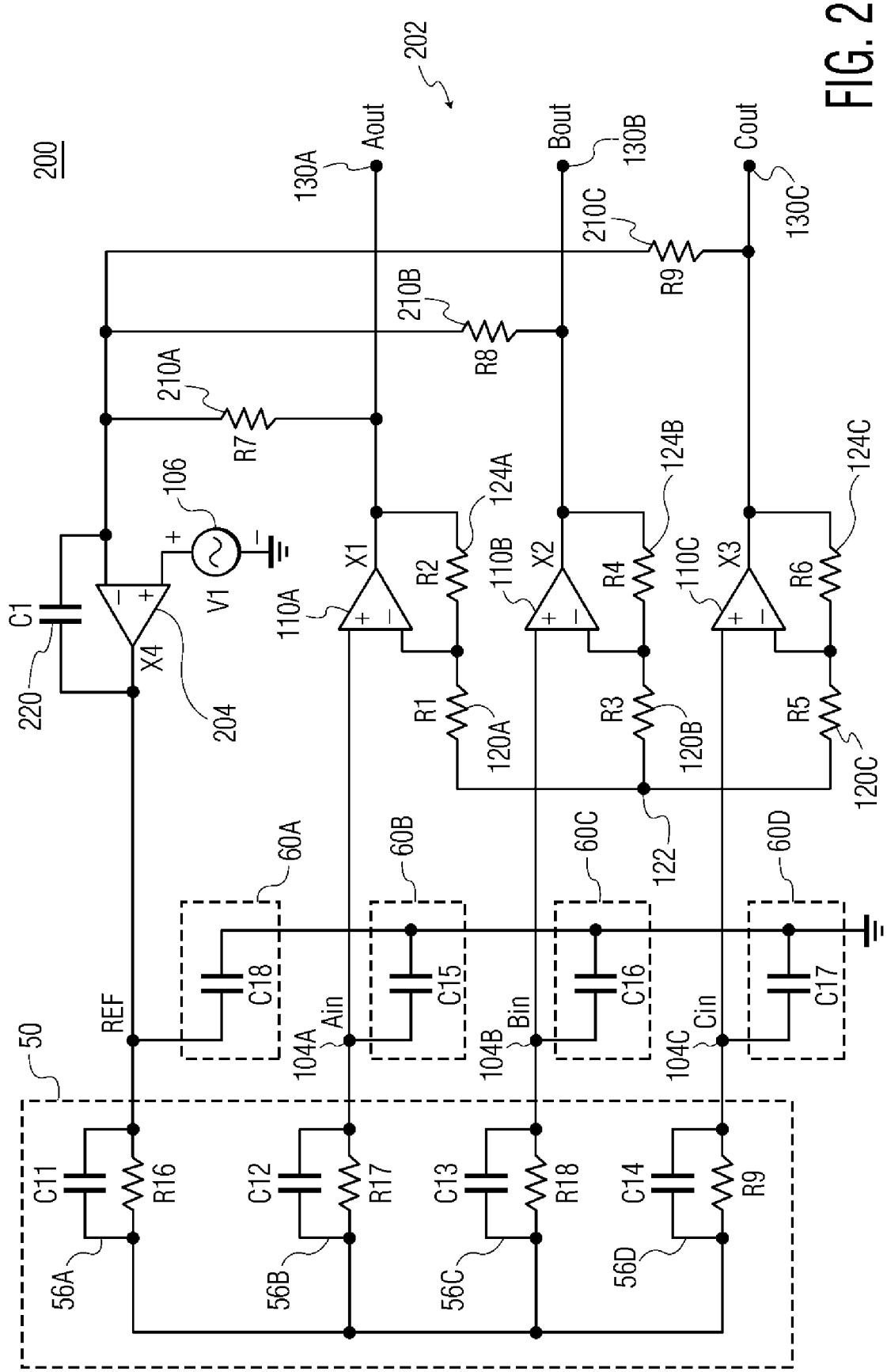
FIG. 2 is a schematic drawing of an electrode contact quality measurement system according to another embodiment of the present invention.

FIG. 2 illustrates an electrode contact quality measurement system 200 according to another embodiment of the present invention. The system 200 includes a differential array amplifier 202 that has components similar to the differential array amplifier 102. Similar components are referenced in FIG. 2 by the same reference numbers as in FIG. 1. The differential array amplifier 202 further includes active feedback circuitry represented by an op-amp 204, resistors 210A-210C, and capacitor 220. As known by those ordinarily skilled in the art, the effect of the active feedback circuitry is to reduce common mode signals at the patient.

In order to inject an AC signal for lead quality detection, the signal generator 106 is connected in series with the reference electrode REF through the active feedback amplifier 204. The active feedback is used to keep the patient's body potential at the same voltage as that of the ECG measuring circuitry. That is, the feedback circuitry actively adjusts the patient voltage so that the common mode signal at the output nodes 130A-130C are equal to the injected signal V1. Since the common mode gain of the amplifier is unity, the common mode signal at inputs nodes 104A-104C are set to equal V1. Operation of the differential array amplifier 202 is the same as that of the differential array amplifier 102 of FIG. 1 but with the added benefit of the active feedback circuitry to reduce common mode noise.

Figure 3:
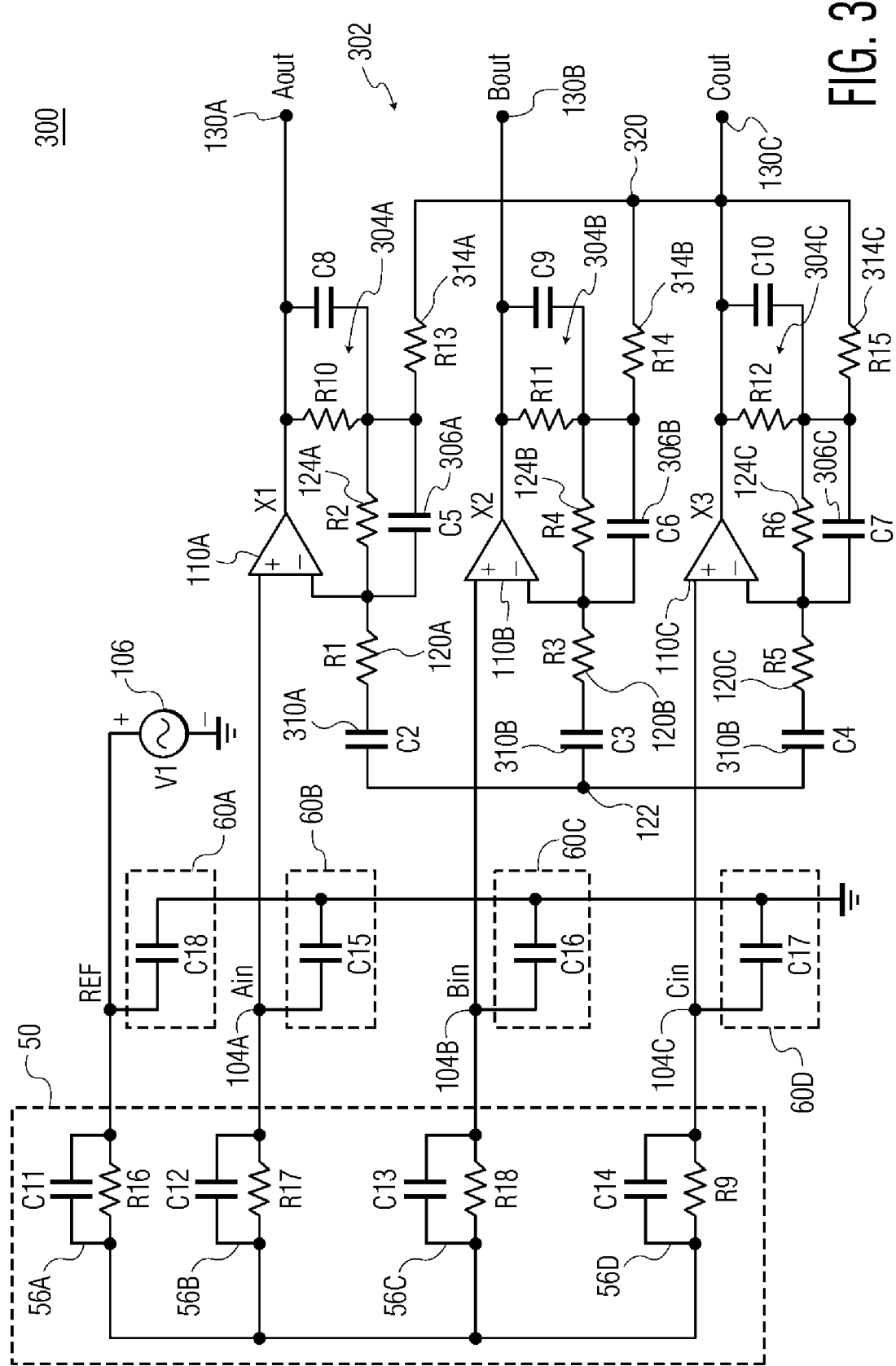
FIG. 3 is a schematic drawing of an electrode contact quality measurement system according to another embodiment of the present invention.

FIG. 3 illustrates an electrode contact quality measurement system 300 according to another embodiment of the present invention. The system 300 includes a differential array amplifier 302 that has similar components as the differential array amplifier 100 of FIG. 1. Similar components shown in FIG. 3 are referenced by the same reference numbers as in FIG. 1. The differential array amplifier 302, however, includes additional circuitry to provide a single pole high pass filter and 2-pole low pass filter.

The high pass filter is provided by coupling capacitors 310A-310C between the common node 122 and the resistors 120A-120C. An ECG circuit needs to tolerate up to 300 mV of DC offset in the electrodes but only +/−5 mV for the actual ECG signal. The high pass filter allows for a much higher differential gain for the +/−5 mV ECG signal without clipping due to the 300 mV DC offset tolerance. The higher differential gain results in improved common mode rejection performance. The improved common mode rejection performance allows for the injected signal V1 to be removed from the ECG unless the input impedance or the patient contact impedance causes a phase shift or attenuation as detected by the differential array amplifier 302. Additionally, the DC level of difference signals at the input nodes 104A-104C can be substantial and the use of a high pass filter will reduce the gain of a DC difference signal to unity gain.

The low pass filter includes a first pole provided by coupling capacitors 306A-306C in parallel with resistors 124A-124C and a second pole provided by resistor-capacitor pairs 304A-304C. Low pass filtering is used to reduce the potential of high frequency signals to alias down to low frequency at the sampling A/D converter.

The differential array amplifier 302 of FIG. 3 further includes another floating common node 320 between the op-amp circuits 110A-110C for each electrode. The floating node 320 behaves in similar fashion as the floating node 122 common to resistors 120A-120C. A common mode signal at an input node 104A-104C will still have unity gain at the output node 130A-130C because the voltage at the floating node 320 will match the input common mode signal due to zero common mode current flowing in resistors 314A-314C.

Figure 4:
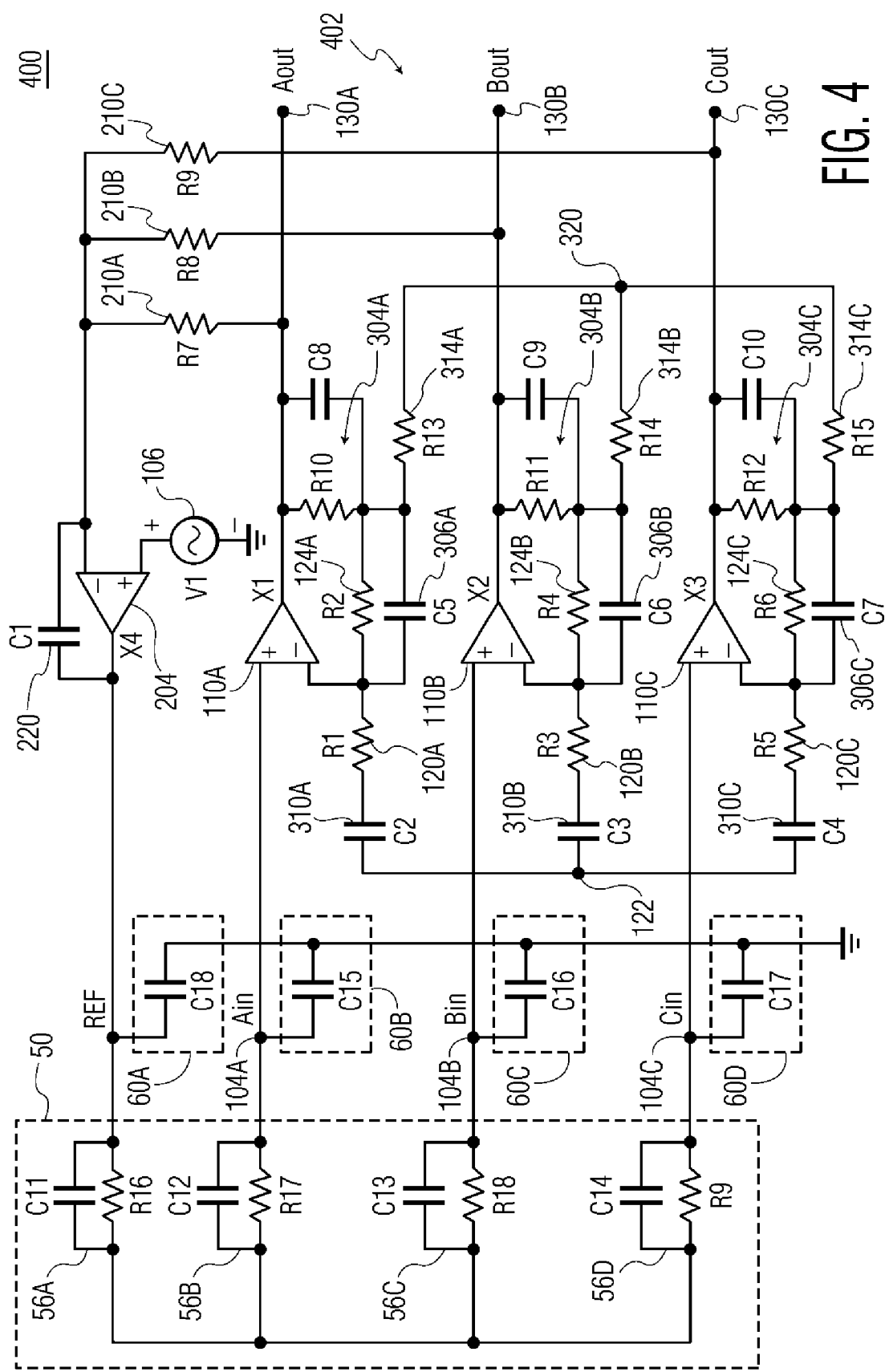
FIG. 4 is a schematic drawing of an electrode contact quality measurement system according to another embodiment of the present invention.

FIG. 4 illustrates an electrode contact quality measurement system 400 according to another embodiment of the present invention. The system 400 includes a differential array amplifier 402 that combines the differential array amplifier 102 (FIG. 1) with both the feedback circuitry of the differential array amplifier 202 (FIG. 2) and the high pass and low pass filters of the differential array amplifier 302 (FIG. 3). Components of the system 400 that are similar with the systems 100, 200, and 300 are referenced in FIG. 4 by the same reference numbers.

As previously discussed, the high pass and low pass filters do not affect the common mode gain. Consequently, the active feedback loop can be designed to have higher loop bandwidth since it is not affected by the differential gain poles and zeroes associated with the differential filters. The differential array amplifier 402 provides significant filtering for out of band rejection and further provides significant amount of common mode rejection.

Figure 5:
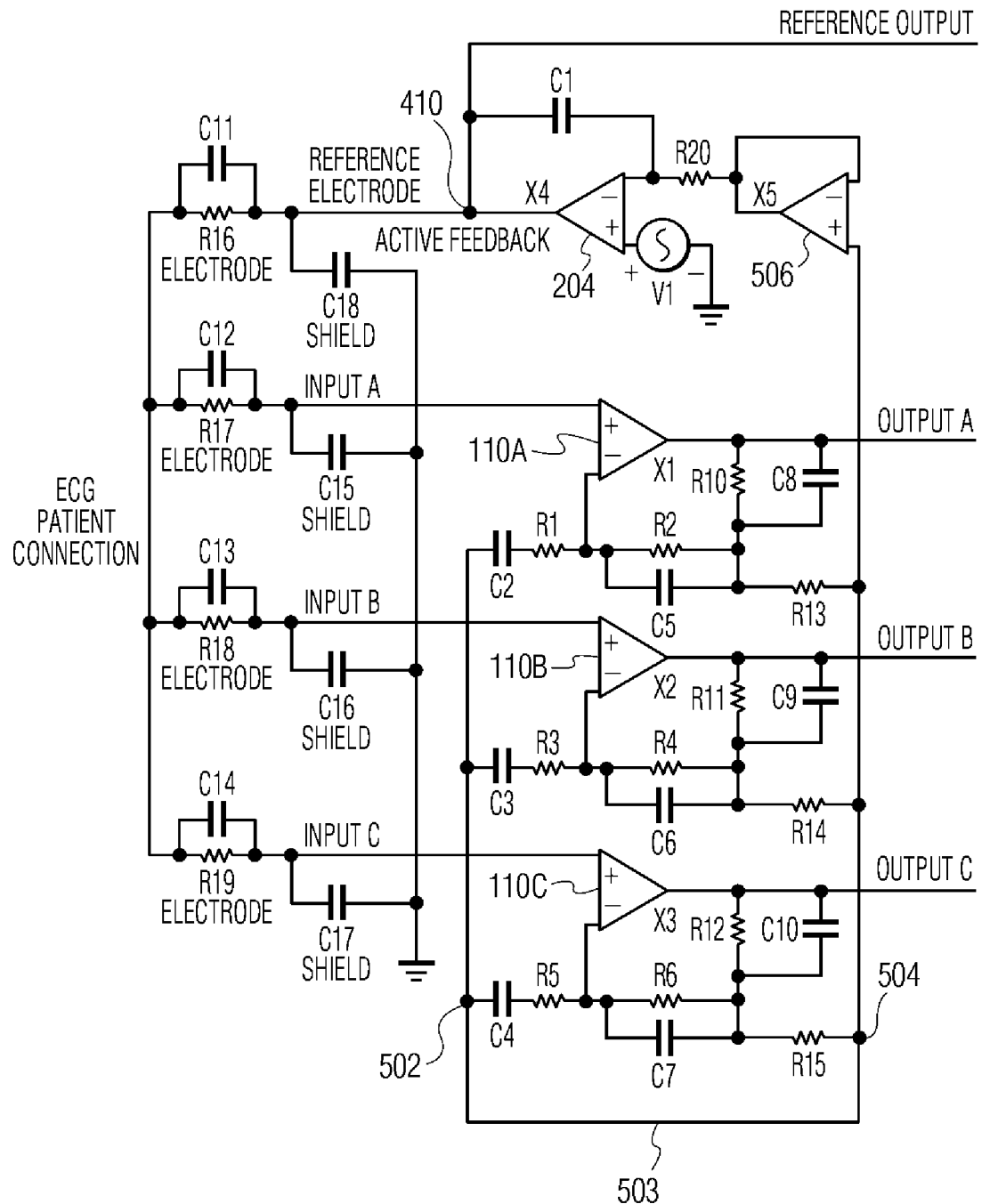
FIG. 5 is a schematic drawing of an electrode contact quality measurement system according to another embodiment of the present invention.

FIG. 5 illustrates another example of electrode circuitry in accordance with the present invention which builds further on the concepts of the previous examples. In this arrangement the common node 502 at the inputs of the electrode channel amplifiers 110A, 110B and 110C is tied to the common node 504 of the feedback path by a connection 503. This connection has been found to provide improved stability in a constructed circuit in which the values of all of the corresponding resistors and capacitors of the multiple channels are not precisely matched. The cost of the arrangement is thus reduced by the ability to use wider tolerance components. Also included is a buffer amplifier 506 between the common feedback output 504 of the electrode channels and the feedback input to the feedback amplifier 204. This embodiment has also been found to provide an output 410 indicative of the quality of attachment of the reference electrode. If the reference electrode contact quality is poor, the signals to the electrode channels are all affected, which is reflected in the buffered feedback signal to the feedback amplifier 204 and in the active feedback signal produced by amplifier 204. A "Reference Output" signal from feedback node 410 thus provides an indication of poor contact by the reference electrode.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A system for generating output signals indicative of contact quality of a plurality of electrodes coupled to a patient, the system comprising:

a signal generator coupled to a reference electrode and operable to output an alternating signal; and a differential array amplifier having a plurality of inputs and a corresponding plurality of differential amplifier stages, each input configured to be coupled to a respective one of the plurality of electrodes, each differential amplifier stage including a differential amplifier having a first input coupled to the respective input, a second input coupled to a first floating common node, and an output coupled to a second floating common node, each differential amplifier stage further including a first capacitor-resistor pair coupled in parallel between the output and the second floating common node, a second capacitor-resistor pair coupled in parallel between the second input and the second floating common node, and a third capacitor-resistor pair coupled in series between the second input and the first floating common node, the differential array amplifier operable to output a respective output signal in response to a respective input signal applied to the respective input, the respective output signal indicative of contact quality for the respective electrode.

2. The system of claim 1 wherein the differential array amplifier further including a feedback amplifier having a first input coupled to the signal generator and an output coupled to the reference electrode, the feedback amplifier further having a second input coupled to the outputs of the plurality of differential amplifiers, each output coupled to the second output of the feedback amplifier through a respective resistor.

3. The system of claim 1 wherein each of the plurality of differential amplifiers are coupled to have a common mode gain of unity.

4. The system of claim 1 wherein the system is included in an ECG measurement system operable to acquire ECG signals.

* * * * *